(12) United States Patent
Chiu et al.

(10) Patent No.: US 8,518,899 B2
(45) Date of Patent: Aug. 27, 2013

(54) MACROCYCLIC POLYMORPHS, COMPOSITIONS COMPRISING SUCH POLYMORPHS AND METHODS OF USE AND MANUFACTURE THEREOF

(75) Inventors: Yu-Hung Chiu, San Diego, CA (US); Tessie Mary Che, San Diego, CA (US); Alex Romero, San Diego, CA (US); Yoshi Ichikawa, San Diego, CA (US); Youe-Kong Shue, San Diego, CA (US)

(73) Assignee: Optimer Pharmaceuticals, Inc., Jersey City, NJ (US)

( * ) Notice: Subject to any disclaimer, the term of this patent is extended or adjusted under 35 U.S.C. 154(b) by 879 days.

(21) Appl. No.: 12/552,919

(22) Filed: Sep. 2, 2009

(65) Prior Publication Data

US 2010/0010076 A1    Jan. 14, 2010

Related U.S. Application Data

(63) Continuation of application No. 12/523,790, filed as application No. PCT/US2008/000735 on Jan. 22, 2008.

(60) Provisional application No. 60/881,950, filed on Jan. 22, 2007.

(51) Int. Cl.
*A61K 31/70*       (2006.01)
*A01N 43/04*       (2006.01)
*C07H 17/08*       (2006.01)

(52) U.S. Cl.
USPC ............................................ 514/28; 536/7.1

(58) Field of Classification Search
USPC ........................................... 514/28; 536/7.1
See application file for complete search history.

(56) References Cited

U.S. PATENT DOCUMENTS 5,583,115 A  *  12/1996  McAlpine et al.  ..............  514/32

FOREIGN PATENT DOCUMENTS

WO    WO 2006085838 A1  *  8/2006

OTHER PUBLICATIONS definition of refer, Dictionary.com, http://dictionary.reference.com/browse/refer, accessed online on Feb. 2, 2012.*
Arnone et al. J. Chem. Soc. Perkins Trans. 1, 1987, p. 1353-1359.*
Davidovich et al. Am. Pharm. Rev., 2004, 7(1), p. 10, 12, 14, 16 and 100.*

* cited by examiner

*Primary Examiner* — Shaojia Anna Jiang
*Assistant Examiner* — Jonathan S Lau
(74) *Attorney, Agent, or Firm* — Morgan Lewis & Bockius LLP

(57) ABSTRACT

The invention relates to novel forms of compounds displaying broad spectrum antibiotic activity, especially crystalline polymorphic forms and amorphous forms of such compounds, compositions comprising such crystalline polymorphic forms and amorphous forms of such compounds, processes for manufacture and use thereof. The compounds and compositions of the invention are useful in the pharmaceutical industry, for example, in the treatment or prevention of diseases or disorders associated with the use of antibiotics, chemotherapies, or antiviral therapies, including, but not limited to, colitis, for example, pseudo-membranous colitis; antibiotic associated diarrhea; and infections due to *Clostridium difficile* ("*C. difficile*"), *Clostridium perfringens* ("*C. perfringens*"), *Staphylococcus* species, for example, methicillin-resistant *Staphylococcus*, or *Enterococcus* including Vancomycin-resistant enterococci.

24 Claims, 3 Drawing Sheets

MACROCYCLIC POLYMORPHS, COMPOSITIONS COMPRISING SUCH POLYMORPHS AND METHODS OF USE AND MANUFACTURE THEREOF

1. RELATED APPLICATIONS

This application is a continuation of pending U.S. application Ser. No. 12/523,790, filed Jul. 20, 2009, which is a U.S. National Phase Application of International Application Number PCT/US2008/000735 filed Jan. 22, 2008, which claims the benefit of U.S. Provisional Patent Application No. 60/881,950, filed Jan. 22, 2007, each of which is incorporated by reference in its entirety.

2. FIELD OF THE INVENTION

The invention encompasses novel forms of compounds displaying broad spectrum antibiotic activity, especially crystalline polymorphic forms and amorphous forms of such compounds, compositions comprising such crystalline polymorphic forms and amorphous forms of such compounds, processes for manufacture and use thereof The compounds and compositions of the invention are useful in the medical and pharmaceutical industry, for example, in the treatment or prevention of diseases or disorders associated with the use of antibiotics, chemotherapies, or antiviral therapies, including, but not limited to, colitis, for example, pseudo-membranous colitis; antibiotic associated diarrhea; and infections due to *Clostridium difficile* ("*C. difficile*"), *Clostridium perfringens* ("*C. perfringens*"), *Staphylococcus* species, for example, methicillin-resistant *Staphylococcus*, or *Enterococcus* including Vancomycin-resistant enterococci.

3. BACKGROUND OF THE INVENTION

Antibiotic-associated diarrhea ("AAD") diseases are caused by toxin producing strains of *C. difficile, Staphylococcus aureus* ("*S. aureus*") including methicillin-resistant *Staphylococcus aureus* ("MRSA") and *C. perfringens*. AAD represents a major economic burden to the healthcare system that is conservatively estimated at $3-6 billion per year in excess hospital costs in the United States alone.

AAD is a significant problem in hospitals and long-term care facilities. *C. difficile* is the leading cause of AAD in the hospital setting, accounting for approximately 20% of cases of AAD and the majority of cases of antibiotic-associated colitis ("AAC"). The rising incidence of *C. difficile* associated diarrhea ("CDAD") has been attributed to the frequent prescribing of broad-spectrum antibiotics to hospitalized patients.

The tiacumicins are a group of 18-membered macrolide antibiotics originally isolated from the fermentation broth of *Dactylosporangium aurantiacum*. The tiacumicins are effective Gram-positive antibiotics. In particular, tiacumicins, specifically Tiacumicin B, show activity against a variety of bacterial pathogens and in particular against *C. difficile*, a Gram-positive bacterium (*Antimicrob. Agents Chemother.*, 1991, 1108-1111). A purification of tiacumicins was carried out in suitable solvents, wherein tiacumicin B exhibited a melting point of 143-145° C. (See, e.g., J. E. Hochlowski, et al., *J. Antibiotics*, vol. XL, no. 5, pages 575-588 (1987)).

The polymorphic behavior of a compound can be of crucial importance in pharmacy and pharmacology. Polymorphs are, by definition, crystals of the same molecule having different physical properties as a result of the order of the molecules in the crystal lattice. The differences in physical properties exhibited by polymorphs affect pharmaceutical parameters such as storage stability, compressibility and density (important in formulation and product manufacturing), and dissolution rates (an important factor in determining bio-availability). Differences in stability can result from changes in chemical reactivity (e.g., differential oxidation, such that a dosage form discolors more rapidly when comprised of one polymorph than when comprised of another polymorph) or mechanical changes (e.g., tablets crumble on storage as a kinetically favored polymorph converts to thermodynamically more stable polymorph) or both (e.g., tablets of one polymorph are more susceptible to breakdown at high humidity). As a result of solubility/dissolution differences, in the extreme case, some polymorphic transitions may result in lack of potency or, at the other extreme, toxicity. In addition, the physical properties of a crystal may be important in processing: for example, one polymorph might be more likely to form solvates or might be difficult to filter and wash free of impurities (i.e., particle shape and size distribution might be different between one polymorph relative to the other).

Each pharmaceutical compound has an optimal therapeutic blood concentration and a lethal concentration. The bio-availability of the compound determines the dosage strength in the drug formulation necessary to obtain the ideal blood level. If the drug can crystallize as two or more polymorphs differing in bio-availability, the optimal dose will depend on the polymorph present in the formulation. Some drugs show a narrow margin between therapeutic and lethal concentrations. Thus, it becomes important for both medical and commercial reasons to produce and market the drug in its most thermodynamically stable polymorph, substantially free of other kinetically favored or disfavored polymorphs.

Thus, there is a clear need to develop safe and effective polymorphs of drugs that are efficacious at treating or preventing disorders associated with bacterial pathogens. The present inventors have identified novel crystalline and amorphous forms of 18-membered macrolide compounds that exhibit broad spectrum antibiotic activity.

4. SUMMARY OF THE INVENTION

The invention encompasses novel crystalline and amorphous forms of the macrolide compounds that are useful in treating or preventing bacterial infections and protozoal infections. In an illustrative embodiment, the novel crystalline and amorphous forms of the macrolide compounds of the invention exhibit broad spectrum antibiotic activity. Thus, surprisingly novel crystalline and amorphous forms of the macrolide compounds have been identified, which act as antibiotics possessing a broad spectrum of activity in treating or preventing bacterial infections and protozoal infections, especially those associated with Gram-positive and Gram-negative bacteria and in particular, Gram-positive bacteria.

In one embodiment, the invention encompasses novel crystalline and amorphous forms of the macrolide of Formula I:

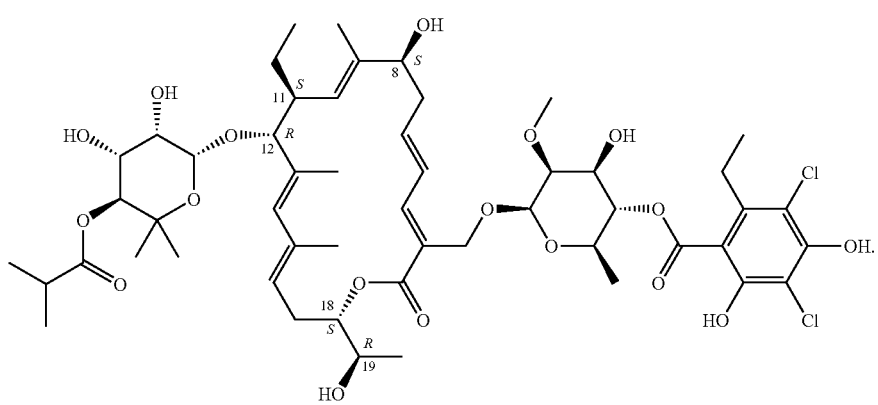

Formula I

In another embodiment, the invention encompasses a mixture of compounds with varying amounts of the Compound of Formula I, which forms have the requisite stability for use in preparing pharmaceutical compositions.

In another embodiment, the invention encompasses a polymorph obtained from a mixture of tiacumicins and a Compound of Formula I.

In still another embodiment, the invention encompasses novel crystalline and amorphous forms of the Compound of Formula I.

In another embodiment, the invention encompasses a pharmaceutical composition comprising a Compound of Formula I.

In another embodiment, the invention encompasses a pharmaceutical composition comprising a Compound of Formula I, wherein the Compound of Formula I is present in an amount greater than 90% by weight.

In another embodiment, the invention encompasses a pharmaceutical composition comprising one or more novel crystalline and amorphous forms of a Compound of Formula I.

In another embodiment, the invention encompasses a pharmaceutical composition comprising a mixture of tiacumicins and Compound of Formula I.

In another embodiment, the invention encompasses a pharmaceutical composition comprising a mixture of tiacumicins and at least about 75% or more by weight of Compound of Formula I. In another embodiment, the invention encompasses a pharmaceutical composition comprising a mixture of tiacumicins and at least about 80% or more by weight of Compound of Formula I. In another embodiment, the invention encompasses a pharmaceutical composition comprising a mixture of tiacumicins and at least about 85% or more by weight of Compound of Formula I. In another embodiment, the invention encompasses a pharmaceutical composition comprising a mixture of tiacumicins and at least about 90% or more by weight of Compound of Formula I. In another embodiment, the invention encompasses a pharmaceutical composition comprising a mixture of tiacumicins and at least about 95% or more by weight of Compound of Formula I. In another embodiment, the invention encompasses a pharmaceutical composition comprising a mixture of tiacumicins and at least about 99% or more by weight of Compound of Formula I.

The invention also encompasses methods for treating or preventing a disease or disorder including, but not limited to, bacterial infections and protozoal infections comprising administering to a subject, preferably a mammal, in need thereof a therapeutically or prophylactically effective amount of a composition or formulation comprising a compound of the invention.

In one illustrative embodiment, the composition or formulation comprises a mixture of compounds with varying amounts of the Compound of Formula I. In another embodiment, the composition or formulation comprises a mixture of tiacumicins and a Compound of Formula I. In still another embodiment, the composition or formulation comprises novel crystalline and amorphous forms of the Compound of Formula I. In still another embodiment, the composition or formulation comprises novel crystalline and amorphous forms of the Compound of Formula I and a mixture of tiacumicins.

In another particular embodiment, the disease or disorder to be treated or prevented are caused by toxin producing strains of *C. difficile, Staphylococcus aureus* ("*S. aureus*") including methicillin-resistant *Staphylococcus aureus* ("MRSA") and *C. perfringens*. In another particular embodiment, the disease or disorder to be treated or prevented is antibiotic-associated diarrhea.

5. BRIEF DESCRIPTION OF THE DRAWINGS

Figure 3:
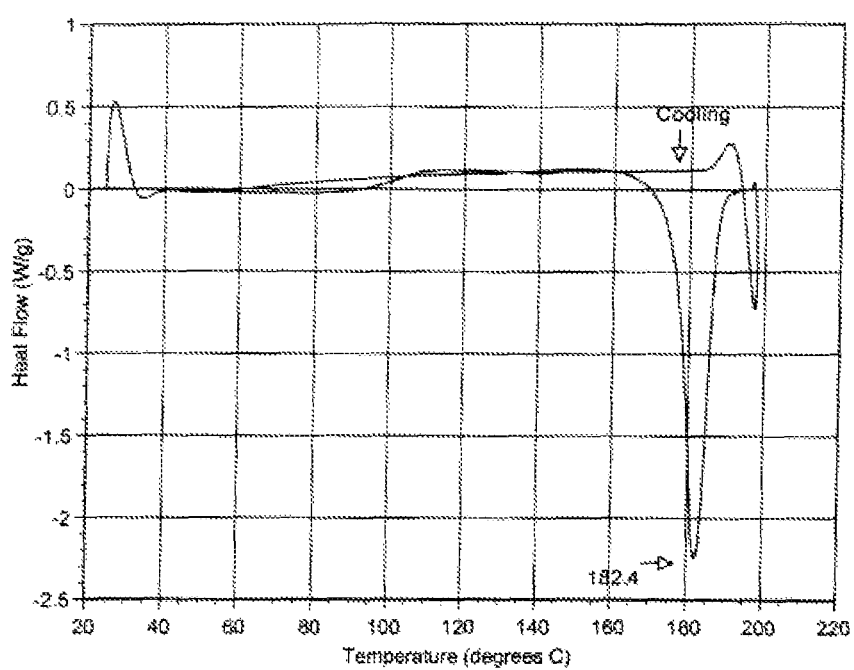

FIG. 3 shows the effect of temperature on a mixture of tiacumicins produced from methanol and water. The DSC indicates an endothermic curve beginning at 169° C., and weight loss beginning at 223° C. The endothermic curve at about 177° C. corresponds to the melting of a first polymorph of a Compound of Formula I.

6. DETAILED DESCRIPTION OF THE DRAWINGS 6.1. General Description

The invention broadly encompasses mixtures of compounds with varying amounts of the Compound of Formula I. The inventors have surprisingly determined that the formation of crystalline polymorphic forms and amorphous forms of a Compound of Formula I and optionally mixtures of tiacumicin depends on the selection of the crystallization solvent and on the method and conditions of crystallization or precipitation.

In one embodiment the invention encompasses a mixture of tiacumicins and a Compound of Formula I. In another embodiment, the invention encompasses novel crystalline and amorphous forms of the Compound of Formula I and optionally a mixture of tiacumicins. In still another embodiment, the invention encompasses novel crystalline and amorphous forms of the Compound of Formula I and a mixture of tiacumicins. In another embodiment, the invention encompasses a mixture of comprising a first polymorph of a Compound of Formula I, a second polymorph of a Compound of Formula I, and other polymorphic forms, amorphous forms and mixtures thereof.

In another particular embodiment, the crystalline polymorphs and amorphous forms are obtained from a mixture of tiacumicins.

In another embodiment, a crystalline polymorph of a Compound of Formula I exhibits a representative powder diffraction pattern comprising at least peaks at the following diffraction angles 2θ of 7.7°, 15.0°, and 18.8°±0.04, preferably ±0.1, more preferably ±0.15, even more preferably ±0.2. In another embodiment, a crystalline polymorph of a Compound of Formula I exhibits a representative powder diffraction pattern comprising at least peaks at the following diffraction angles 2θ of 7.8°, 15.1°, and 18.8°±0.04, preferably ±0.1, more preferably ±0.15, even more preferably ±0.2.

In another embodiment, the polymorph has the chemical structure:

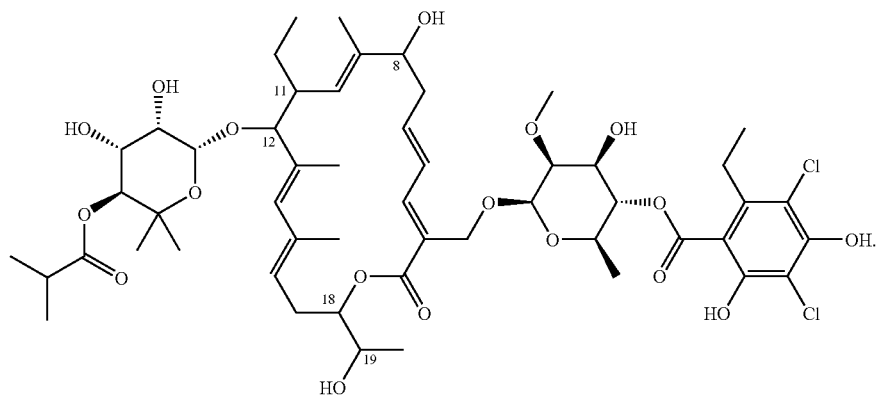

In another embodiment, the polymorph has the chemical structure of a Compound of Formula I:

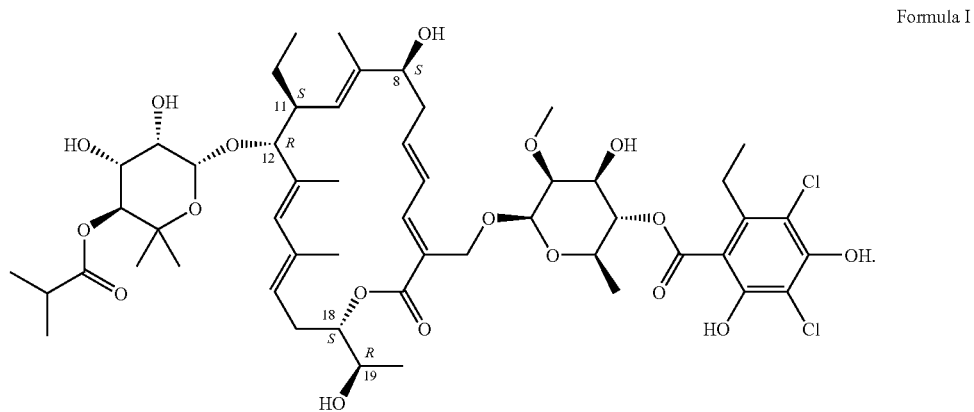

Formula I

In another embodiment, the polymorph further comprises at least one compound selected from a mixture of tiacumicins.

In another embodiment, the polymorph of Formula I is present in an amount from at least about 75% to about 99.99%.

In another embodiment, the polymorph of Formula I is present in an amount of at least about 75%.

In another embodiment, the polymorph of Formula I is present in an amount of at least about 80%.

In another embodiment, the polymorph of Formula I is present in an amount of at least about 85%.

In another embodiment, the polymorph of Formula I is present in an amount of at least about 90%.

In another embodiment, the polymorph of Formula I is present in an amount of at least about 93%.

In another embodiment, the polymorph of Formula I is present in an amount of at least about 95%.

In another embodiment, the polymorph of Formula is present in an amount of at least about 99%.

diffraction angles 2θ of 7.4°, 15.5°, and 18.8°±0.2 and exhibits a melting point of about 150° C. to about 156° C.

Another embodiment of the invention encompasses pharmaceutical compositions comprising a therapeutically or prophylactically effective amount of a crystalline polymorph of a Compound of Formula:

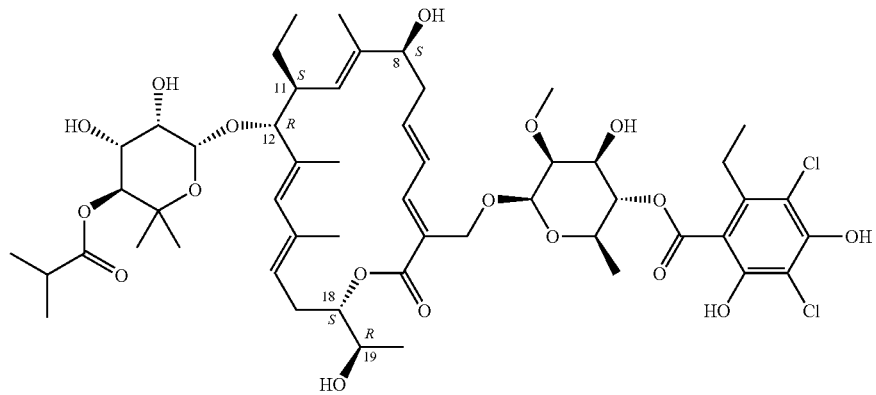

In another embodiment, the crystalline polymorph is obtained from a mixture of tiacumicins that exhibits a melting point of about 163° C. to about 169° C. In another embodiment, the crystalline polymorph is obtained from a mixture of tiacumicins that exhibits a melting point of about 160° C. to about 170° C. In another embodiment, the crystalline polymorph is obtained from a mixture of tiacumicins that exhibits a melting point of about 155° C. to about 175° C.

In another embodiment, the crystalline polymorph is obtained from a mixture of tiacumicins and exhibits a DSC endotherm in the range of about 174° C. to about 186° C.; preferably 175-185° C.

In another embodiment, the crystalline polymorph is obtained from a mixture of tiacumicins that exhibits a powder diffraction pattern comprising at least peaks at the following diffraction angles 2θ of 7.7°, 15.0°, and 18.8°±0.04, preferably ±0.1, more preferably ±0.15, even more preferably ±0.2 and exhibits a melting point of about 163° C. to about 169° C.

In another embodiment, the crystalline polymorph is obtained from a mixture of tiacumicins that exhibits a powder diffraction pattern comprising at least peaks at the following diffraction angles 2θ of 7.7°, 15.0°, and 18.8°±0.04, preferably ±0.1, more preferably ±0.15, even more preferably ±0.2 and exhibits a melting point of about 160° C. to about 170° C.

Another embodiment encompasses a crystalline polymorph obtained from a mixture of tiacumicins that exhibits a powder diffraction pattern comprising at least peaks at the following diffraction angles 2θ of 7.7°, 15.0°, and 18.8°±0.04, preferably ±0.1, more preferably ±0.15, even more preferably ±0.2. In a particular embodiment, the polymorph has the chemical structure of a Compound of Formula I. In another embodiment, the crystalline polymorph further comprises at least one compound selected from a mixture of tiacumicins.

In another embodiment, a crystalline polymorph is obtained from a mixture of tiacumicins that exhibits a melting point of about 150° C. to about 156° C.

In another embodiment, a crystalline polymorph is obtained from a mixture of tiacumicins that exhibits a powder diffraction pattern comprising at least peaks at the following and a pharmaceutically acceptable carrier.

In a particular embodiment, the pharmaceutical composition comprises a first polymorph of a Compound of Formula I, a second polymorph of a Compound of Formula I, other polymorphic forms of a Compound of Formula I, amorphous forms of a Compound of Formula I, and mixtures thereof.

In another embodiment, the crystalline polymorph of the pharmaceutical composition has peaks at the following diffraction angles 2θ of 7.7°, 15.0°, and 18.8°±0.04, preferably ±0.1, more preferably ±0.15, even more preferably ±0.2.

In another embodiment, the crystalline polymorph of the pharmaceutical composition further comprises at least one compound selected from a mixture of tiacumicins.

In another embodiment, the Compound of Formula I is present from at least about 75% to about 99.99%, preferably about 75%, about 85%, about 95%, or about 99%.

In another embodiment, the crystalline polymorph of the pharmaceutical composition exhibits a melting point of about 163° C. to about 169° C.

Another embodiment encompasses a pharmaceutical composition comprising a crystalline polymorph of tiacumicin comprising peaks at the following diffraction angles 2° of 7.6°, 15.4°, and 18.8°±0.04, preferably ±0.1, more preferably ±0.5, even more preferably ±0.2. In a particular embodiment, the pharmaceutical composition further comprises at least one compound selected from a mixture of tiacumicins. In another particular embodiment, the Compound of Formula I is present from about 75% to about 99.99%, preferably 75%, 85%, 95%, or 99%.

In another embodiment, the invention encompasses a pharmaceutical composition containing stereomerically pure R-Tiacumicin and less than 15% of a mixture of tiacumicins. In another embodiment, the invention encompasses a pharmaceutical composition containing stereomerically pure R-Tiacumicin and less than 10% of a mixture of tiacumicins. In another embodiment, the invention encompasses a pharmaceutical composition containing stereomerically pure R-Tiacumicin and less than 7% of a mixture of tiacumicins. In another embodiment, the invention encompasses a pharmaceutical composition containing stereomerically pure R-Tiacumicin and less than 5% of a mixture of tiacumicins. In another embodiment, the invention encompasses a pharmaceutical composition containing stereomerically pure R-Tiacumicin and less than 1% of a mixture of tiacumicins. In another embodiment, the invention encompasses a pharmaceutical composition containing stereomerically pure R-Tiacumicin and less than 15% of a mixture of S-Tiacumicin. In another embodiment, the invention encompasses a pharmaceutical composition containing stereomerically pure R-Tiacumicin and less than 10% of a mixture of S-Tiacumicin. In another embodiment, the invention encompasses a pharmaceutical composition containing stereomerically pure R-Tiacumicin and less than 7% of a mixture of S-Tiacumicin. In another embodiment, the invention encompasses a pharmaceutical composition containing stereomerically pure R-Tiacumicin and less than 5% of a mixture of S-Tiacumicin. In another embodiment, the invention encompasses a pharmaceutical composition containing stereomerically pure R-Tiacumicin and less than 1% of a mixture of S-Tiacumcnicin. In another embodiment, the invention encompasses a pharmaceutical composition containing stereomerically pure R-Tiacumicin and less than 15% of a mixture of Lipiarmycin A4. In another embodiment, the invention encompasses a pharmaceutical composition containing stereomerically pure R-Tiacumicin and less than 10% of a mixture of Lipiarmycin A4. In another embodiment, the invention encompasses a pharmaceutical composition containing stereomerically pure R-Tiacumicin and less than 7% of a mixture of Lipiarmycin A4. In another embodiment, the invention encompasses a pharmaceutical composition containing stereomerically pure R-Tiacumicin and less than 5% of a mixture of Lipiarmycin A4. In another embodiment, the invention encompasses a pharmaceutical composition containing stereomerically pure R-Tiacumicin and less than 1% of a mixture of Lipiarmycin A4.

In another embodiment, the crystalline polymorph of the pharmaceutical composition exhibits a melting point of about 153° C. to about 156° C.

In another embodiment, the therapeutically or prophylactically effective amount is from about 0.01 mg/kg to about 1000 mg/kg, preferably 0.01, 0.1, 1, 2.5, 5, 10, 20, 50, 100, 250, or 500 mg/kg.

In another embodiment, the crystalline polymorph of the pharmaceutical composition is suitable for parenteral administration, preferably intravenous, intramuscular, or intraarterial.

In another embodiment, the crystalline polymorph of the pharmaceutical composition is suitable for peroral administration.

Another embodiment of the invention encompasses a method for treating a bacterial infection comprising administering a pharmaceutical composition comprising a polymorph of the invention to a subject in need thereof.

In a particular embodiment, the bacterial infection is in the gastrointestinal tract, particularly AAC or AAD.

6.2. Definitions

The term "antibiotic-associated condition" refers to a condition resulting when antibiotic therapy disturbs the balance of the microbial flora of the gut, allowing pathogenic organisms such as enterotoxin producing strains of *C. difficile, S. aureus* and *C. perfringens* to flourish. These organisms can cause diarrhea, pseudomembranous colitis, and colitis and are manifested by diarrhea, urgency, abdominal cramps, tenesmus, and fever among other symptoms. Diarrhea, when severe, causes dehydration and the medical complications associated with dehydration.

The term "asymmetrically substituted" refers to a molecular structure in which an atom having four tetrahedral valences is attached to four different atoms or groups. The commonest cases involve the carbon atom. In such cases, two optical isomers (D- and L-enantiomers or R- and S-enantiomers) per carbon atom result which are nonsuperposable mirror images of each other. Many compounds have more than one asymmetric carbon. This results in the possibility of many optical isomers, the number being determined by the formula 2n, where n is the number of asymmetric carbons.

The term "broth" as used herein refers to the fluid culture medium as obtained during or after fermentation. Broth comprises a mixture of water, the desired antibiotic(s), unused nutrients, living or dead organisms, metabolic products, and the adsorbent with or without adsorbed product.

As used herein and unless otherwise indicated, the terms "bacterial infection(s)" and "protozoal infection(s)" are used interchangeably and include bacterial infections and protozoal infections that occur in mammals, fish and birds as well as disorders related to bacterial infections and protozoal infections that may be treated or prevented by antibiotics such as the Compounds of the Invention. Such bacterial infections and protozoal infections, and disorders related to such infections, include the following: disorders associated with the use of antibiotics, chemotherapies, or antiviral therapies, including, but not limited to, colitis, for example, pseudo-membranous colitis, antibiotic associated diarrhea, and infections due to *Clostridium difficile, Clostridium perfringens, Staphylococcus* species, methicillin-resistant *Staphylococcus*, or *Enterococcus* including Vancomycin-resistant enterococci; antibiotic-associated diarrhea including those caused by toxin producing strains of *C. difficile, S. aureus* including methicillin-resistant *Staphylococcus aureus*, and *C. perfringens*; and antibiotic-associated colitis; pneumonia, otitis media, sinusitis, bronchitis, tonsillitis and mastoiditis related to infection by *Staphylococcus pneumoniae, Haemophilus influenzae, Moraxella catarrhalis, Staphlococcus aureus*, or *Peptostreptococcus* spp.; pharyngitis, rheumatic fever and glomerulonephritis related to infection by *Streptococcus pyogenes*, Groups C and G streptococci, *Clostridium diptheriae*, or *Actinobacillus haemolyticum*; respiratory tract infections related to infection by *Mycoplasma pneumoniae, Legionella pneumophila, Streptococcus pneumoniae, Haemophilus influenzae*, or *Chlamydia pneumoniae*; uncomplicated skin and soft tissue infections, abscesses and osteomyelitis, and puerperal fever related to infection by *Staphlococcus aureus*, coagulase-positive staphlococci (e.g., *S. epidermis* and *S. hemolyticus*), *Staphylococcus pyogenes, Streptococcus agalactiae, Streptococcal* groups C-F (minute-colony streptococci), viridans streptococci, *Corynebacterium minutissimum, Clostridium* spp., or *Bartonella henselae*; uncomplicated acute urinary tract infections related to infection by *Staphylococcus saprophyticus* or *Enterococcus* spp.; urethritis and cervicitis; and sexually transmitted diseases related to infection by *Chlamydia trachomatis, Haemophilus ducreyi, Treponema pallidum, Ureaplasma urealyticum*, or *Neiserria gonorrhea*; toxin diseases related to infection by *S. aureus* (food poisoning and Toxic Shock Syndrome), or Groups A, B and C streptococci; ulcers related to infection by *Helicobacterpylori*, systemic febrile syndromes related to infection by *Borrelia recurrentis*; Lyme disease related to infection by *Borrelia burgdorferi*, conjunctivitis, keratitis, and dacrocystitis related to infection by *Chlamydia trachomatis, Neisseria gonorrhoeae, S. aureus, S. pneumoniae*, S. pyogenes, H. influenzae, or Listeria spp.; disseminated Mycobacterium avium complex (MAC) disease related to infection by Mycobacterium avium, or Mycobacterium intracellulare; gastroenteritis related to infection by Campylobacter jejuni; intestinal protozoa related to infection by Cryptosporidium spp.; odontogenic infection related to infection by viridans streptococci; persistent cough related to infection by Bordetella pertussis; gas gangrene related to infection by Clostridium perfringens or Bacteroides spp.; and atherosclerosis related to infection by Helicobacter pylori or Chlamydia pneumoniae. Bacterial infections and protozoal infections and disorders related to such infections that may be treated or prevented in animals include the following: bovine respiratory disease related to infection by P. haem., P. multocida, Mycoplasma bovis, or Bordetella spp.; cow enteric disease related to infection by E. coli or protozoa (e.g., coccidia, cryptosporidia, etc.); dairy cow mastitis related to infection by Staph. aureus, Strep. uberis, Strep. agalactiae, Strep. dysgalactiae, Klebsiella spp., Corynebacterium, or Enterococcus spp.; swine respiratory disease related to infection by A. pleura., P. multocida or Mycoplasma spp.; swine enteric disease related to infection by E. coli Lawsonia intracellularis, Salmonella, or Serpulina hyodyisinteriae; cow footrot related to infection by Fusobacterium spp.; cow metritis related to infection by E. coli; cow hairy warts related to infection by Fusobacterium necrophorum or Bacteroides nodosus; cow pink-eye related to infection by Moraxella bovis; cow premature abortion related to infection by protozoa (e.g., neosporium)-urinary tract infection in dogs and cats related to infection by E. coli; skin and soft tissue infections in dogs and cats related to infection by Staph, epidermidis, Staph. intermedius, coagulase neg. Staph. or P. multocida; and dental or mouth infections in dogs and cats related to infection by Alcaligenes spp., Bacteroides spp., Clostridium spp., Enterobacter spp., Eubacterium, Peptostreptococcus, Porphyromonas, or Prevotella. Other bacterial infections and protozoal infections and disorders related to such infections that may be treated or prevented in accord with the methods of the invention are referred to in Sanford, J. P., et al., "The Sanford Guide To Antimicrobial Therapy," 27$^{th}$ Edition (Antimicrobial Therapy, Inc., 1996).

As used herein and unless otherwise indicated, the term "binders" refers to agents used to impart cohesive qualities to the powdered material. Binders, or "granulators" as they are sometimes known, impart cohesiveness to the tablet formulation, which insures the tablet remaining intact after compression, as well as improving the free-flowing qualities by the formulation of granules of desired hardness and size. Materials commonly used as binders include starch; gelatin; sugars, such as sucrose, glucose, dextrose, molasses, and lactose; natural and synthetic gums, such as acacia, sodium alginate, extract of Irish moss, panwar gum, ghatti gum, mucilage of isapol husks, carboxymethylcellulose, methylcellulose, polyvinylpyrrolidone, Veegum, microcrystalline cellulose, microcrystalline dextrose, amylose, and larch arabogalactan, and the like.

As used herein and unless otherwise indicated, the terms "biohydrolyzable amide," "biohydrolyzable ester," "biohydrolyzable carbamate," "biohydrolyzable carbonate," "biohydrolyzable ureide," "biohydrolyzable phosphate" mean an amide, ester, carbamate, carbonate, ureide, or phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, lower acyloxyalkyl esters (such as acetoxylmethyl, acetoxyethyl, aminocarbonyloxy-methyl, pivaloyloxymethyl, and pivaloyloxyethyl esters), lactonyl esters (such as phthalidyl and thiophthalidyl esters), lower alkoxyacyloxyalkyl esters (such as methoxycarbonyloxy-methyl, ethoxycarbonyloxyethyl and isopropoxycarbonyloxyethyl esters), alkoxyalkyl esters, choline esters, and acylamino alkyl esters (such as acetamidomethyl esters). Examples of biohydrolyzable amides include, but are not limited to, lower alkyl amides, a amino acid amides, alkoxyacyl amides, and alkylaminoalkyl-carbonyl amides. Examples of biohydrolyzable carbamates include, but are not limited to, lower alkylamines, substituted ethylenediamines, aminoacids, hydroxyalkylamines, heterocyclic and heteroaromatic amines, and polyether amines.

As used herein and unless otherwise indicated, the term "carrier" refers to a diluent, adjuvant, excipient, or vehicle with which a composition is administered. Such pharmaceutical carriers can be sterile liquids, such as water and oils, including those of petroleum, animal, vegetable or synthetic origin, such as peanut oil, soybean oil, mineral oil, sesame oil and the like.

As used herein and unless otherwise indicated, the term "Compounds of the Invention" means, collectively, a Compound of Formula I and/or pharmaceutically acceptable salts and polymorphs thereof The compounds of the invention are identified herein by their chemical structure and/or chemical name. Where a compound is referred to by both a chemical structure and a chemical name, and that chemical structure and chemical name conflict, the chemical structure is determinative of the compound's identity. The compounds of the invention may contain one or more chiral centers and/or double bonds and, therefore, exist as stereoisomers, such as double-bond isomers (i.e., geometric isomers), enantiomers, or diastereomers. According to the invention, the chemical structures depicted herein, and therefore the compounds of the invention, encompass all of the corresponding compound's enantiomers and stereoisomers, that is, both the stereomerically pure form (e.g., geometrically pure, enantiomerically pure, or diastereomerically pure) and enantiomeric and stereoisomeric mixtures. Enantiomeric and stereoisomeric mixtures can be resolved into their component enantiomers or stereoisomers by well known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically- or enantiomerically-pure intermediates, reagents, and catalysts by well known asymmetric synthetic methods. The Compounds of the Invention are preferably substantially stereomerically pure. In a particular embodiment, the term "Compounds of the Invention" refers to a Compound of Formula that is greater than 75% pure, preferably greater than 85% pure, more preferably greater than 95% pure and most preferably greater than 99% pure and polymorphic form (e.g., a polymorph of Compound of Formula I) and amorphous forms thereof.

As used herein and unless otherwise indicated, "diluents" are inert substances added to increase the bulk of the formulation to make the tablet a practical size for compression. Commonly used diluents include calcium phosphate, calcium sulfate, lactose, kaolin, mannitol, sodium chloride, dry starch, powdered sugar, silica, and the like.

As used herein and unless otherwise indicated, "disintegrators" or "disintegrants" are substances that facilitate the breakup or disintegration of tablets after administration. Materials serving as disintegrants have been chemically classified as starches, clays, celluloses, algins, or gums. Other disintegrators include Veegum HV, methylcellulose, agar, bentonite, cellulose and wood products, natural sponge, cation-exchange resins, alginic acid, guar gum, citrus pulp, cross-linked polyvinylpyrrolidone, carboxymethylcellulose, and the like.

When administered to a subject (e.g., to an animal for veterinary use or to a human for clinical use) the compounds of the invention are administered in isolated form. As used herein and unless otherwise indicated, "isolated" means that the compounds of the invention are separated from other components of either (a) a natural source, such as a plant or cell, preferably bacterial culture, or (b) a synthetic organic chemical reaction mixture, preferably, via conventional techniques, the compounds of the invention are purified. As used herein, "purified" means that when isolated, the isolate contains at least about 70% preferably at least about 80%, more preferably at least about 90%, even more preferably at least about 95%, and most preferably at least about 99% of a compound of the invention by weight of the isolate.

The term "macrolide" or "macrocycle" refers to organic molecules with large ring structures usually containing over 10 atoms.

The term "18-membered macrocycles" refers to organic molecules with ring structures containing 18 atoms.

The term "MIC" or "minimum inhibitory concentration" refers to the lowest concentration of an antibiotic that is needed to inhibit growth of a bacterial isolate in vitro. A common method for determining the MIC of an antibiotic is to prepare several tubes containing serial dilutions of the antibiotic, that are then inoculated with the bacterial isolate of interest. The MIC of an antibiotic can be determined from the tube with the lowest concentration that shows no turbidity (no growth).

The term "MIC50" refers to the lowest concentration of antibiotic required to inhibit the growth of 50% of the bacterial strains tested within a given bacterial species.

The term "MIC90" refers to the lowest concentration of antibiotic required to inhibit the growth of 90% of the bacterial strains tested within a given bacterial species.

As used herein and unless otherwise indicated, the term "mixture of tiacumicins" refers to a composition containing at least one macrolide compound from the family of compounds known tiacumicins. In another embodiment, the term "mixture of tiacumicins" includes a mixture containing at least one member of the compounds known tiacumicins and a Compound of Formula I, wherein the Compound of Formula I is present in an amount of about 50%, 60%, 70%, 80%, 90%, 95%, 99%, 99.9%, or 99.99% by weight. In particular, the term "mixture of tiacumicins" refers to a compositions comprising a Compound of Formula I, wherein the Compound of Formula I has a relative retention time ("RTT") ratio of 1.0, and further comprising at least one of the following compounds:

Compound 101

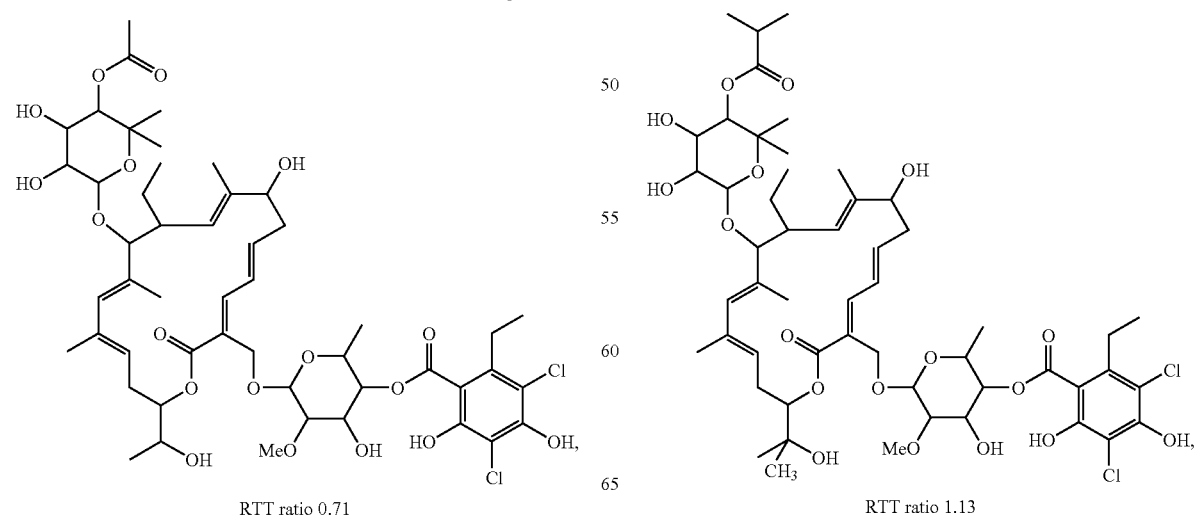

RTT ratio 0.71

Compound 102

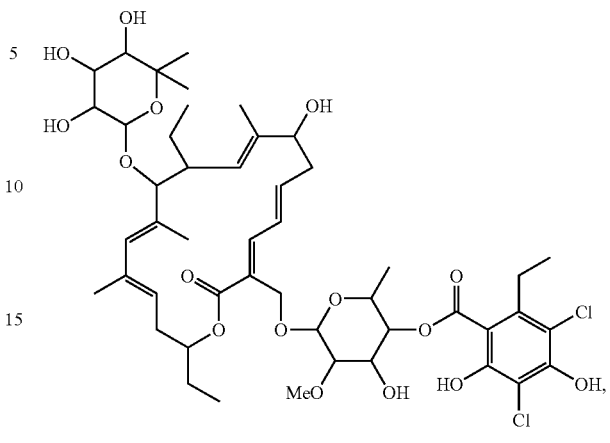

RTT ratio 0.81

Compound 103

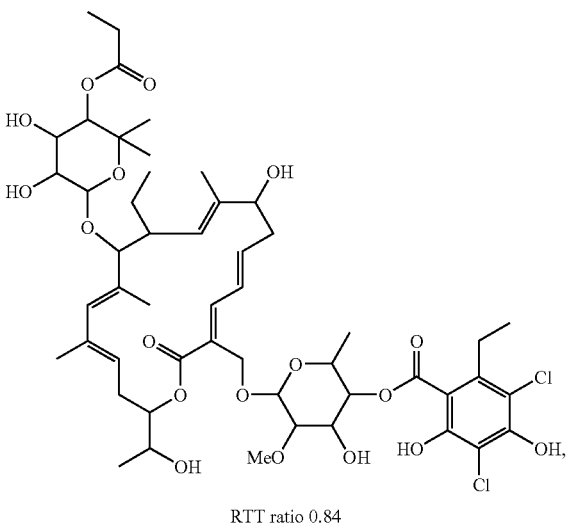

RTT ratio 0.84

Compound 104

RTT ratio 1.13

Compound 105
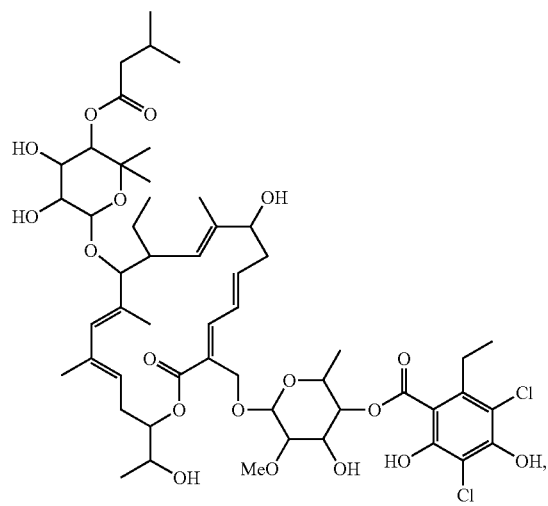
RTT ratio 1.19
Compound 106
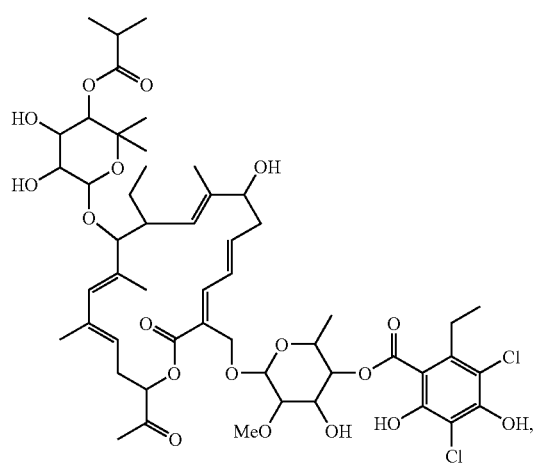
RTT ratio 1.24
Compound 107
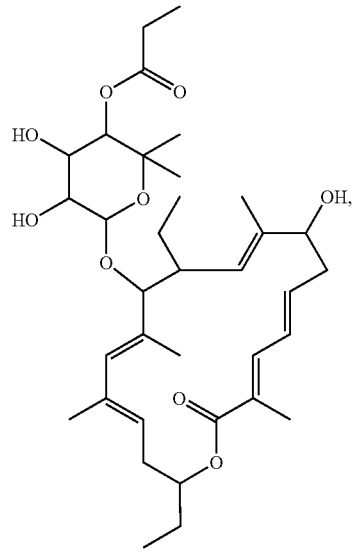
RTT ratio 1.39
Compound 108
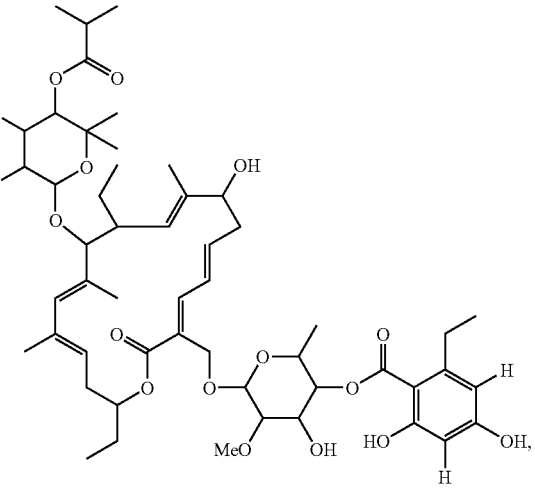
RTT ratio 1.48
Compound 109
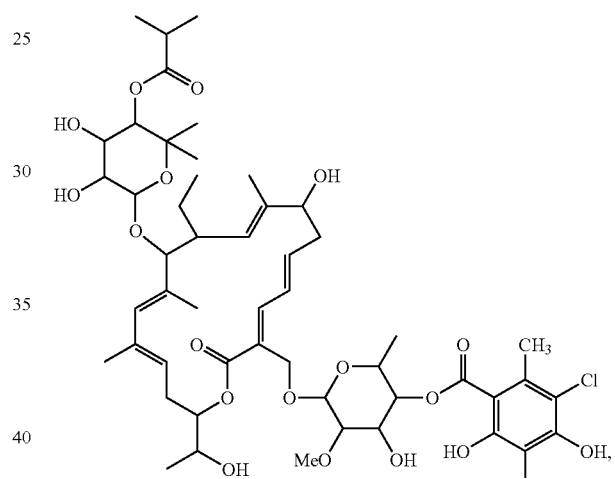
RTT ratio 0.89
Compound 110
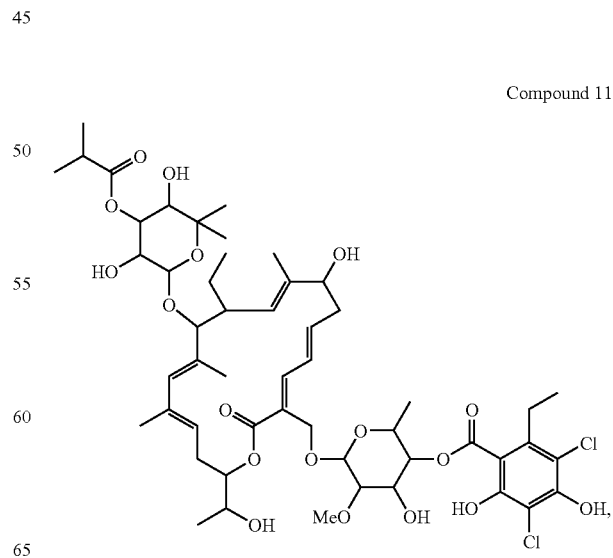
RTT ratio 0.92

-continued

Compound 111

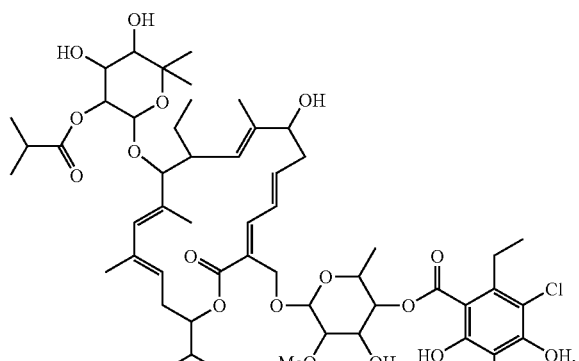

RTT ratio 0.95

Compound 112

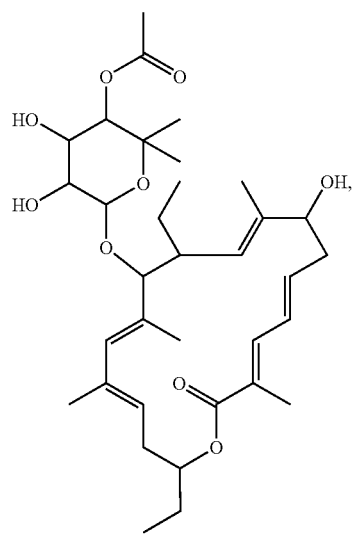

RTT ratio 1.10

In certain illustrative embodiments, when compound 109 is present in the mixture optionally one of compounds 110, 111, and/or 112 is also present in the mixture. Compound 109 is also sometimes referred to as Lipiarmycin A4. Compound 110 is also sometimes referred to as Tiacumicin F. Compound 111 is also sometimes referred to as Tiacumicin C. Compound 112 is also sometimes referred to as Tiacumicin A.

As used herein, and unless otherwise indicated, the terms "optically pure," "stereomerically pure," and "substantially stereomerically pure" are used interchangeably and mean one stereoisomer of a compound or a composition that comprises one stereoisomer of a compound and is substantially free of other stereoisomer(s) of that compound. For example, a stereomerically pure compound or composition of a compound having one chiral center will be substantially free of the opposite enantiomer of the compound. A stereomerically pure compound or composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound.

As used herein and unless otherwise indicated, "pharmaceutically acceptable" refers to materials and compositions that are physiologically tolerable and do not typically produce an allergic or similar untoward reaction, such as gastric upset, dizziness and the like, when administered to a human. Typically, as used herein, the term "pharmaceutically acceptable" means approved by a regulatory agency of the Federal or a state government or listed in the U.S. Pharmacopeia or other generally recognized pharmacopeia for use in animals, and more particularly in humans.

As used herein and unless otherwise indicated, the term "pharmaceutically acceptable hydrate" means a Compound of the Invention that further includes a stoichiometric or non-stoichiometric amount of water bound by non-covalent intermolecular forces.

As used herein and unless otherwise indicated, the term "pharmaceutically acceptable polymorph" refers to a Compound of the Invention that exists in several distinct forms (e.g., crystalline, amorphous), the invention encompasses all of these forms.

As used herein and unless otherwise indicated, the term "pharmaceutically acceptable prodrug" means a derivative of a modified polymorph of a compound of Formula I that can hydrolyze, oxidize, or otherwise react under biological conditions (in vitro or in vivo) to provide the compound. Examples of prodrugs include, but are not limited to, compounds that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include compounds that comprise oligonucleotides, peptides, lipids, aliphatic and aromatic groups, or NO, $NO_2$, ONO, and $ONO_2$ moieties. Prodrugs can typically be prepared using well known methods, such as those described in Burger's Medicinal Chemistry and Drug Discovery, 172 178, 949 982 (Manfred E. Wolff ed., 5th ed. 1995), and Design of Prodrugs (H. Bundgaard ed., Elsevier, New York 1985).

The phrase "pharmaceutically acceptable salt(s)," as used herein includes but is not limited to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions including, but not limited to, sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds, included in the present compositions, which are acidic in nature are capable of forming base salts with various pharmacologically acceptable cations. Examples of such salts include alkali metal or alkaline earth metal salts and, particularly, calcium, magnesium, sodium lithium, zinc, potassium, and iron salts.

As used herein and unless otherwise indicated, the term "prophylactically effective" refers to an amount of a Compound or Composition of the Invention or a pharmaceutically acceptable salt, solvate, polymorph, or prodrug thereof causing a reduction of the risk of acquiring a given disease or disorder. Accordingly, the Compounds of the Invention may be used for the prevention of one disease or disorder and concurrently treating another (e.g., prevention of AAC, while treating urinary AAD). In certain embodiments, the compositions of the invention are administered to a patient, preferably a human, as a preventative measure against such diseases. As used herein, "prevention" or "preventing" refers to a reduction of the risk of acquiring a given disease or disorder.

As used herein, the term "subject" can be a mammal, preferably a human or an animal. The subject being treated is a patient in need of treatment.

As used herein and unless otherwise indicated, the phrase "therapeutically effective amount" of a Compound or Composition of the Invention or a pharmaceutically acceptable salt, solvate, polymorph, or prodrug thereof is measured by the therapeutic effectiveness of a compound of the invention, wherein at least one adverse effect of a disorder is ameliorated or alleviated. In one embodiment, the term "therapeutically effective amount" means an amount of a drug or Compound of the Invention that is sufficient to provide the desired local or systemic effect and performance at a reasonable benefit/risk ratio attending any medical treatment. In one embodiment, the phrase "therapeutically effective amount" of a composition of the invention is measured by the therapeutic effectiveness of a compound of the invention to alleviate at least one symptom associated with bacterial or protazoal infections. Surprisingly, the inventors have found that therapeutically effective amounts of the compounds of the invention are useful in treating or preventing bacterial and protazoal infections.

As used herein and unless otherwise indicated, the terms "treatment" or "treating" refer to an amelioration of a disease or disorder, or at least one discernible symptom thereof, preferably associated with a bacterial or protozoal infection. In another embodiment, "treatment" or "treating" refers to an amelioration of at least one measurable physical parameter, not necessarily discernible by the patient. In yet another embodiment, "treatment" or "treating" refers to inhibiting the progression of a disease or disorder, either physically, e.g., stabilization of a discernible symptom, physiologically, for example, stabilization of a physical parameter, or both. In yet another embodiment, "treatment" or "treating" refers to delaying the onset of a disease or disorder.

6.3. Compositions of the Invention for Therapeutic/Prophylactic Administration The invention encompasses compositions comprising a first polymorph of a Compound of Formula I, a second polymorph of a Compound of Formula I, other polymorphic forms, amorphous form or mixtures thereof of a mixture of tiacumicins with varying amounts of the Compound of Formula I.

The invention further encompasses an antibiotic composition that is a mixture of tiacumicins for use in treating CDAD as well as, AAD and AAC. The mixture of tiacumicins contains about 76 to about 100% of a Compound of Formula I, which belongs to the tiacumicin family of 18-member macrolide.

Due to the activity of the Compounds of the Invention, the compounds are advantageously useful in veterinary and human medicine. The Compounds of the Invention are useful for the treatment or prevention of bacterial and protozoal infections. In some embodiments, the subject has an infection but does not exhibit or manifest any physiological symptoms associated with an infection.

The invention provides methods of treatment and prophylaxis by administration to a patient of a therapeutically effective amount of a composition comprising a crystalline polymorph or amorphous form of a Compound of the Invention. The patient is a mammal, including, but not limited, to an animal such a cow, horse, sheep, pig, chicken, turkey, quail, cat, dog, mouse, rat, rabbit, guinea pig, etc., and is more preferably a human.

The present compositions, which comprise one or more crystalline polymorph or amorphous form of a Compounds of the Invention or a mixture of tiacumicins may be administered by any convenient route, for example, peroral administration, parenteral administration, by infusion or bolus injection, by absorption through epithelial or mucocutaneous linings (e.g., oral mucosa, rectal and intestinal mucosa, etc.) and may be administered together with another biologically active agent. Administration can be systemic or local. Various delivery systems are known, e.g., encapsulation in liposomes, microparticles, microcapsules, capsules, etc., and can be used to administer a compound of the invention. In certain embodiments, more than one Compound of the Invention and mixture of tiacumicins is administered to a patient. Methods of administration include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The preferred mode of administration is left to the discretion of the practitioner, and will depend in-part upon the site of the medical condition. In most instances, administration will result in the release of the crystalline polymorph or amorphous form of a Compound of the Invention into the bloodstream.

In specific embodiments, it may be desirable to administer one or more crystalline polymorph or amorphous form of a Compound of the Invention locally to the area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of an atherosclerotic plaque tissue.

Pulmonary administration can also be employed, e.g., by use of an inhaler or nebulizer, and formulation with an aerosolizing agent, or via perfusion in a fluorocarbon or synthetic pulmonary surfactant. In certain embodiments, the compounds of the invention can be formulated as a suppository, with traditional binders and vehicles such as triglycerides.

In another embodiment, the a crystalline polymorph or amorphous form of a Compound of the Invention can be delivered in a vesicle, in particular a liposome (see Langer, 1990, Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

In yet another embodiment, the compounds of the invention can be delivered in a controlled release system. In one embodiment, a pump may be used (see Langer, supra; Sefton, 1987, *CRC Crit. Ref. Biomed. Eng.* 14:201; Buchwald et al., 1980, *Surgery* 88:507 Saudek et al., 1989, N. Engl. J. Med. 321:574). In another embodiment, polymeric materials can be used (see *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, New York (1984); Ranger and Peppas, 1983, *J. Macromol. Sci. Rev. Macromol. Chem.* 23:61; see also Levy et al., 1985, *Science* 228:190; During et al., 1989, *Ann Neurol.* 25:351; Howard et al., 1989, *J. Neurosurg.* 71:105). In yet another embodiment, a controlled-release system can be placed in proximity of the target of the compounds of the invention, e.g., the liver, thus requiring only a fraction of the systemic dose (see, e.g., Goodson, in *Medical Applications of Controlled Release*, supra, vol. 2, pp. 115-138 (1984)). Other controlled-release systems discussed in the review by Langer, 1990, Science 249:1527-1533) may be used.

The present compositions will contain a therapeutically effective amount of a crystalline polymorph or amorphous form of a Compound of the Invention, optionally more than one crystalline polymorph or amorphous form of a Compound of the Invention, preferably in purified form, together with a suitable amount of a pharmaceutically acceptable vehicle so as to provide the form for proper administration to the patient.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "vehicle" refers to a diluent, adjuvant, excipient, or carrier with which a compound of the invention is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used. When administered to a patient, the compounds of the invention and pharmaceutically acceptable vehicles are preferably sterile. Water is a preferred vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., U.S. Pat. No. 5,698,155). Other examples of suitable pharmaceutical vehicles are described in "Remington's Pharmaceutical Sciences" by A. R. Gennaro.

In a preferred embodiment, the crystalline polymorph or amorphous form of a Compound of the Invention is formulated in accordance with routine procedures as a pharmaceutical composition adapted for intravenous administration to human beings. Typically, a crystalline polymorph or amorphous form of a Compound of the Invention for intravenous administration is a solution in sterile isotonic aqueous buffer. Where necessary, the compositions may also include a solubilizing agent. Compositions for intravenous administration may optionally include a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the crystalline polymorph or amorphous form of a Compound of the Invention is to be administered by infusion, it can be dispensed, for example, with an infusion bottle containing sterile pharmaceutical grade water or saline. Where the compound of the invention is administered by injection, an ampoule of sterile water for injection or saline can be provided so that the ingredients may be mixed prior to administration.

It is preferred that the compositions of the invention be administered orally. Compositions for oral delivery may be in the form of tablets, lozenges, aqueous or oily suspensions, granules, powders, emulsions, capsules, syrups, or elixirs, for example. Orally administered compositions may contain one or more optionally agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions may be coated to delay disintegration and absorption in the gastrointestinal tract thereby providing a sustained action over an extended period of time. Selectively permeable membranes surrounding an osmotically active driving compound are also suitable for orally administered crystalline polymorph or amorphous form of a Compound of the Invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

The amount of a crystalline polymorph or amorphous form of a Compound of the Invention that will be effective in the treatment of a particular disorder or condition disclosed herein will depend on the nature of the disorder or condition, and can be determined by standard clinical techniques. In addition, in vitro or in vivo assays may optionally be employed to help identify optimal dosage ranges. The precise dose to be employed in the compositions will also depend on the route of administration, and the seriousness of the disease or disorder, and should be decided according to the judgment of the practitioner and each patient's circumstances. However, suitable dosage ranges for oral administration are generally about 0.001 milligram to 1000 milligrams of a compound of the invention per kilogram body weight. In specific preferred embodiments of the invention, the oral dose is 0.01 milligram to 500 milligrams per kilogram body weight, more preferably 0.1 milligram to 100 milligrams per kilogram body weight, more preferably 0.5 milligram to 50 milligrams per kilogram body weight, and yet more preferably 1 milligram to 10 milligrams per kilogram body weight. In a most preferred embodiment, the oral dose is 1 milligram of a crystalline polymorph or amorphous form of a Compound of the Invention per kilogram body weight. The dosage amounts described herein refer to total amounts administered; that is, if more than one compound of the invention is administered, the preferred dosages correspond to the total amount of the compounds of the invention administered. Oral compositions preferably contain 10% to 95% active ingredient by weight.

Suitable dosage ranges for intravenous (i.v.) administration are 0.001 milligram to 1000 milligrams per kilogram body weight, 0.1 milligram to 100 milligrams per kilogram body weight, and 1 milligram to 10 milligrams per kilogram body weight. Suitable dosage ranges for intranasal administration are generally about 0.01 pg/kg body weight to 1 mg/kg body weight. Suppositories generally contain 0.01 milligram to 50 milligrams of a compound of the invention per kilogram body weight and comprise active ingredient in the range of 0.5% to 10% by weight. Recommended dosages for intradermal, intramuscular, intraperitoneal, subcutaneous, epidural, sublingual, intracerebral, intravaginal, transdermal administration or administration by inhalation are in the range of 0.001 milligram to 1000 milligrams per kilogram of body weight. Suitable doses of the compounds of the invention for topical administration are in the range of 0.001 milligram to 1 milligram, depending on the area to which the compound is administered. Effective doses may be extrapolated from dose-response curves derived from in vitro or animal model test systems. Such animal models and systems are well known in the art.

The invention also provides pharmaceutical packs or kits comprising one or more containers filled with one or more crystalline polymorph or amorphous form of a Compound of the Invention. Optionally associated with such container(s) can be a notice in the form prescribed by a governmental agency regulating the manufacture, use or sale of pharmaceuticals or biological products, which notice reflects approval by the agency of manufacture, use or sale for human administration. In a certain embodiment, the kit contains more than one crystalline polymorph or amorphous form of a Compound of the Invention.

The crystalline polymorph or amorphous form of a Compound of the Invention is preferably assayed in vitro and in vivo, for the desired therapeutic or prophylactic activity, prior to use in humans. For example, in vitro assays can be used to determine whether administration of a specific compound of the invention or a combination of compounds of the invention is preferred for lowering fatty acid synthesis. The compounds of the invention may also be demonstrated to be effective and safe using animal model systems.

Other methods will be known to the skilled artisan and are within the scope of the invention.

6.4. General Synthesis of the Compounds of the Invention

The 18-membered macrocycles and analogs thereof are produced by fermentation. Cultivation of *Dactylosporangium aurantiacum* subspecies *hamdenensis* AB 718C-41 NRRL 18085 for the production of the tiacumicins is carried out in a medium containing carbon sources, inorganic salts and other organic ingredients with one or more absorbents under proper aeration conditions and mixing in a sterile environment.

The microorganism to produce the active antibacterial agents was identified as belonging to the family Actinoplanaceae, genus *Dactylosporangium* (*J. Antibiotics*, 1987, 40: 567-574 and U.S. Pat. No. 4,918,174). It has been designated *Dactylosporangium aurantiacum* subspecies *hamdenensis* 718C-41. The subculture was obtained from the ARS Patent Collection of the Northern Regional Research Center, United States Department of Agriculture, 1815 North University Street, Peoria, Ill. 61604, U.S.A., where it was assigned accession number NRRL 18085. The characteristics of strain AB 718C-41 are given in the *Journal of Antibiotics*, 1987, 40: 567-574 and U.S. Pat. No. 4,918,174.

This invention encompasses the composition of novel antibiotic agents, Tiacumicins, by submerged aerobic fermentation of the microorganism *Dactylosporangium aurantiacum* subspecies *hamdenensis*. The production method is disclosed in WO 2004/014295 A2, which is hereby incorporated by reference.

7. Examples

7.1. Preparation of the Crude Mixtures of Tiacumicins and the Subsequent Crystallization of Certain Polymorphs of the Mixtures In an illustrative embodiment, a mixture of tiacumicins containing the Compound of Formula I is prepared by a process comprising:
   (i); culturing a microorganism in a nutrient medium to accumulate the mixture in the nutrient medium; and
   (ii) isolating the mixture from the nutrient medium; wherein the nutrient medium comprises an adsorbent to adsorb the mixture.

The nutrient medium preferably comprises from about 0.5 to about 15% of the adsorbent by weight. The absorbent is preferably an adsorbent resin. More preferably, the adsorbent resin is Amberlite®, XAD16, XAD16HP, XAD2, XAD7HP, XAD1180, XAD1600, IRC50, or Duolite® XAD761. The microorganism is preferably *Dactylosporangium aurantiacum* subspecies *hamdenensis*. The nutrient medium comprises the following combination based on weight: from about 0.2% to about 10% of glucose, from about 0.02% to about 0.5% of $K_2HPO_4$, from about 0.02% to about 0.5% of $MgSO_4 \cdot 7H_2O$, from about 0.01% to about 0.3% of KCl, from about 0.1% to about 2% of $CaCO_3$, from about 0.05% to about 2% of casamino acid, from about 0.05% to about 2% of yeast extract, and from about 0.5% to about 15% of XAD-16 resin. The culturing step is preferably conducted at a temperature from about 25° C. to about 35° C. and at a pH from about 6.0 to about 8.0.

Upon completion of fermentation, the solid mass (including the adsorbent resin) is separated from the broth by sieving. The solid mass is eluted with organic solvents such as, for example, ethyl acetate then concentrated under reduced pressure.

7.2. Structure of R-Tiacumicin B

The structure of the R-Tiacumicin B (the major most active component) is shown below in Forumla I. The X-ray crystal structure of the R-Tiacumicin B was obtained as a colorless, parallelpiped-shaped crystal (0.08×0.14×0.22 mm) grown in aqueous methanol. The x-ray structure confirms the structure shown below. The official chemical name is 3-[[[6-Deoxy-4-O-(3,5-dichloro-2-ethyl-4,6-dihydroxybenzoyl)-2-O-methyl-β-D-mannopyranosyl]oxy]-methyl]-12(R)-[[6-deoxy-5-C-methyl-4-O-(2-methyl-1-oxopropyl)-β-D-lyxo-hexopyranosyl]oxy]-11(S)-ethyl-8(S)-hydroxy-18(S)-(1 (R)-hydroxyethyl)-9,13,15-trimethyloxacyclooctadeca-3,5,9,13,15-pentaene-2-one.

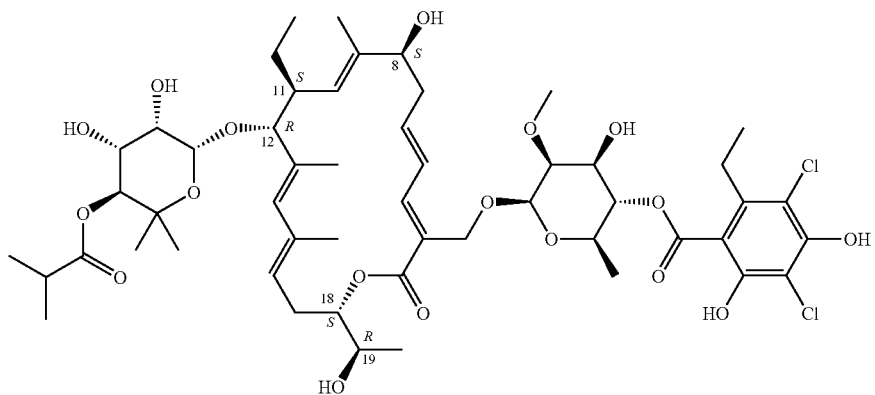

7.2.1 Analytical Data of R-Tiacumicin B

The analytical data of R-Tiacumicin B (which is almost entirely (i.e., >90%) R-Tiacumicin).

mp 166-169° C. (white needle from isopropanol);
$[\alpha]_D^{20}$-6.9 (c 2.0, MeOH);
MS m/z (ESI) 1079.7 (M+Na)$^+$;
$^1$H NMR (400 MHz, CD$_3$OD) δ 7.21 (d, 1H), 6.59 (dd, 1H), 5.95 (ddd, 1H), 5.83 (br s, 1H), 5.57 (t, 1H), 5.13 (br d, 1H), 5.09 (t, 1H), 5.02 (d, 1H), 4.71 (m, 1H), 4.71 (br s, 1H), 4.64 (br s, 1H), 4.61 (d, 1H), 4.42 (d, 1H), 4.23 (m, 1H), 4.02 (pentet, 1H), 3.92 (dd, 1H), 3.73 (m, 2H), 3.70 (d, 1H), 3.56 (s, 3H), 3.52-3.56 (m, 2H), 2.92 (m, 2H), 2.64-2.76 (m, 3H), 2.59 (heptet, 1H), 2.49 (ddd, 1H), 2.42 (ddd, 1H), 2.01 (dq, 1H), 1.81 (s, 3H), 1.76 (s, 3H), 1.65 (s, 3H), 1.35 (d, 3H), 1.29 (m, 1H), 1.20 (t, 3H), 1.19 (d, 3H), 1.17 (d, 3H), 1.16 (d, 3H), 1.14 (s, 3H), 1.12 (s, 3H), 0.87 (t, 3H);
$^{13}$C NMR (100 MHz, CD$_3$OD) δ 178.4, 169.7, 169.1, 154.6, 153.9, 146.2, 143.7, 141.9, 137.1, 137.0, 136.4, 134.6, 128.5, 126.9, 125.6, 124.6, 114.8, 112.8, 108.8, 102.3, 97.2, 94.3, 82.5, 78.6, 76.9, 75.9, 74.5, 73.5, 73.2, 72.8, 71.6, 70.5, 68.3, 63.9; 62.2, 42.5, 37.3, 35.4, 28.7, 28.3, 26.9, 26.4, 20.3, 19.6, 19.2, 18.7, 18.2, 17.6, 15.5, 14.6, 14.0, 11.4.

7.3. Preparation of a First Polymorph of R-Tiacumicin B

Another illustrative embodiment of the invention comprises a process for producing a polymorph of a Compound of Formula I from a mixture of tiacumicins comprising the steps of:

a) dissolving a crude mixture of tiacumicins containing from about 76% to about 100% of a Compound of Formula I in a minimum amount of solution comprising methanol, water, acetonitrile, acetic acid, or isopropyl alcohol mixtures thereof;
b) allowing the solution of a) to evaporate while standing at room temperature (e.g., about 22° C.) for 3 to 7 days to precipitate a first polymorph of a Compound of Formula I; and
c) separating the polymorph from the solution by techniques known in the art.

7.3.1. Illustrative Example 1 of the Preparation of a Polymorph of R-Tiacumicin B After the fermentation process as described for example in Section 7.1., the crude material was purified by reverse phase chromatography using a Biotage Flash 75L system containing a 1.2 kg, Biotage KP-C18-HS silica column, eluted with 70:30:1, MeOH/H$_2$O/AcOH. The collected fractions containing 75-80% of Compound of Formula I were combined and concentrated to one-third of the original volume to produce a precipitate. The precipitate is filtered and washed with water. The solid was dried under high vacuum to afford an off-white powder. HPLC analysis showed the powder contains about 78% of Compound of Formula I as a major product and a mixture of tiacumicins as the minor component.

The mixture of tiacumicins containing about 78% of Compound of Formula I (i.e., 50 mg) was dissolved in 2 mL of methanol followed by addition of 1 mL of water. The solution was allowed to evaporate, while standing at room temperature for 7 days to produce a crystalline precipitate. The crystal is separated from the solution by filtration. After methanol/water recrystallization, the crystals contain about 90% of Compound of Formula I based on HPLC.

7.3.2. Illustrative Example 2 of the Preparation of a Polymorph of R-Tiacumicin After the fermentation process as described for example in Section 7.1., the crude material was purified by reverse phase chromatography using a Biotage Flash 150 system containing a 3.75 kg, Biotage KP-C18-HS silica column, eluted with 52:48:1, EtOH/H$_2$O/AcOH. The collected fractions containing about 80-88% of Compound of Formula I were combined and concentrated to one-third the original volume to produce a precipitate. The precipitate was filtered and washed with water. The solid was dried under high vacuum. HPLC analysis showed the powder contains 85.4% of Compound of Formula I as a major product and a mixture of tiacumicins as the minor component.

The mixture containing about 85% of Compound of Formula I (i.e., 1000 mg) was dissolved in 20 mL of a mixture of methanol and water at ratios 1:1 methanol water. The solution was allowed to evaporate/stand at room temperature for 3 days to produce a polymorph crystalline precipitate. The crystal was separated from the solution by filtration.

The composition obtained is a mixture containing a first polymorph of a Compound of Formula I, and at least one of the tiacumicin compounds based on HPLC analysis. The composition has a melting point of 165-169° C.

7.3.3. Illustrative Example 3 of the Preparation of a Poylmorph of R-Tiacumicin After the fermentation process as described for example in Section 7.1., the crude material was purified by reverse phase chromatography using a Biotage Flash 75L system containing a 1.2 kg, Biotage KP-C18-HS silica column, eluted with MeOH/H$_2$O/AcOH 67:33:4 to 70:30:1. The collected fractions containing>90% of Compound of Formula I was combined and concentrated to one-third volume. The precipitate was filtered and washed with water. The solid was dried under high vacuum. HPLC analysis showed the powder contains 94.0% of Compound of Formula I.

The solid was tested by X-ray diffraction (XRD) and Differential Scanning Calorimetry (DSC). The X-ray diffraction of the solid shows peaks at angles 2θ of 7.7°, 15.0°, and 18.8°±0.1 indicating the solid is the form of a first polymorph of a Compound of Formula I. The DSC plot shows and endothermic curve starting at about at 168° C. and peak at 177®C.

73.4. Illustrative Example 4 of the Preparation of a Polymorph of R-Tiacumicin After the fermentation process as described for example in Section 7.1., the crude material was purified by reverse phase chromatography using a Biotage Flash 75L system containing a 1.2 kg, Biotage KP-C18-HS silica column, eluted with 52:48:1, EtOH/H$_2$O/AcOH. The collected fractions containing>90% of Compound of Formula I were combined, one-third volume of water was added and left at room temperature overnight. The precipitate was filtered and washed with water. The solid was dried under high vacuum. HPLC analysis showed the powder contains 94.7% of Compound of Formula I.

The powder containing 94.7% of Compound of Formula I (i.e., 98 mg) was dissolved in 3 mL of methanol and then 1 mL of water was added. The solution was allowed to evaporate and stand at room temperature for 7 days to produce a crystalline precipitate. The crystals were separated from the solution by filtration and washed with methanol/water 3:1. The crystals were analyzed by X-ray diffraction.

Composition of the precipitate is a mixture comprising a Compound of Formula I based on HPLC analysis with a melting point of 166-169° C.

7.3.5. Illustrative Example 5 of the Preparation of a Polymorph of R-Tiacumicin After the fermentation process as described for example in Section 7.1., the mixture was purified on a column, and a 0.06 gm of a mixture of tiacumicins was dissolved in 16 mL of methanol and 4 mL of water in a 20 mL vial. The vial is covered with parafilm, and pinholes were punched through. The covered vial is placed in a desiccator and stored at room temperature for ten days. Parafilm cover is then removed, and the vial is returned to desiccator. Crystalline material is produced within three to five days after the parafilm is removed. The crystalline material is washed with a solution of methanol and water and the Compound of Formula I was isolated in 75.6%.

X-ray powder diffraction pattern of the crystalline material is shown in FIG. 3 included 2θ of 7.7°, 15.0°, and 18.0°.

7.3.6. Illustrative Example 6 of the Preparation of a Polymorph of R-Tiacumicin Preparation of a Polymorph from Isopropanol
After the fermentation process as described for example in Section 7.1., the crude material was purified by reverse phase chromatography using a Biotage Flash 150 system containing a 3.75 kg, Biotage KP-C18-HS silica column, eluted with 52:48:1, EtOH/H$_2$O/AcOH. The collected fractions containing 80-88% of Compound of Formula I were combined and concentrated to one-third of the original volume to produce a precipitate. The precipitate was filtered and washed with water. The solid was dried under high vacuum. HPLC analysis showed the powder contains 85.4% of Compound of Formula I.

The powder containing 85.4% Compound of Formula I (i.e., 2000 mg) was dissolved in 900 mL of isopropanol. The solution was heated to increase solubility and then filtered to remove insoluble materials. The clear solution was allowed to evaporate/stand at room temperature for 14 days to produce a crystalline precipitate. The crystal is separated from the solution by filtration.

Composition of the precipitate is a mixture comprising Compound of Formula I and at least one of other related substances based on HPLC analysis with mp of 163-165° C.

X-ray diffraction of the precipitate shows peaks at angles 2θ of 7.6° and 15.4°.

7.3.7. Illustrative Example 7 of the Preparation of a Polymorph of R-Tiacumicin After the fermentation process as described for example in Section 7.1., and column purification, a mixture of Compound of Formula I, >90%, 15 g) was dissolved in minimum amount of methanol (from about 20 mL to about 30 mL), the solution was triturated with isopropanol (~100 mL) to produce a polymorph. The solid is separated from the solution by filtration with melting point of 165-168° C.

The XRD diagram shows a distinct polymorph pattern comprising 2 theta values of 7.5°, 15.2°, 15.7°, 18.6° 18.7°.

7.3.8. Illustrative Example 5 of the Preparation of a Polymorph of R-Tiacumicin Preparation of a Polymorph from Acetonitrile
The mixture of tiacumicins obtained as described above and (85.44% of Compound of Formula I, 1000 mg) was dissolved in 30 mL of acetonitrile. The solution was allowed to evaporate and stand at room temperature for 12 days to produce a crystalline precipitate. The crystal is separated from the solution by filtration, and exhibits a melting point of 165-169° C.

The XRD diagram of this crystal shows the pattern of a polymorph comprising 2 theta values of 7.8°, 15.1°, 18.8°.

7.4. Preparation of Other Polymorphs of R-Tiacumicin

Another illustrative embodiment of the invention comprises a process for producing a polymorph of a Compound of Formula I comprising the steps of:
a) dissolving crude mixture of tiacumicins containing from about 78 to about 100% of a Compound of Formula I in a minimum amount of ethyl acetate;
b) allowing the solution to evaporate and stand at room temperature for 3 to 7 days to precipitate a polymorph; and
c) separating polymorph from the solution

7.4.1. Illustrative Example 1 of the Preparation of a Polymorph of R-Tiacumicin Preparation of Polymorph from Ethyl Acetate
After the fermentation process as described for example in Section 7.1., the crude material was purified by reverse phase chromatography using a Biotage Flash 150 system containing a 3.75 kg, Biotage KP-C18-HS silica column, eluted with 52:48:1, EtOH/H$_2$O/AcOH. The collected fractions containing 70-88% of Compound of Formula I was combined and concentrated to one-third volume to produce a precipitate. The precipitate is filtered and washed with water. The solid was dried under high vacuum. HPLC analysis showed the powder contains 85.4% of Compound of Formula I.

This crude tiacumicin mixture (1000 mg) was then dissolved in 30 mL of ethyl acetate. The solution was allowed to evaporate and stand at room temperature for 12 days to produce a crystalline precipitate of Polymorph B of the Compound of Formula I. The crystals were separated from the solution by filtration. The crystals have a melting point of about 153-156° C., which confirm a different polymorphic form from the first polymorph.

7.4.2. Illustrative Example 2 of the Preparation of a Polymorph of R-Tiacumicin Preparation of a Polymorph from Methanol and Isopropanol.

After the fermentation process as described for example in Section 7.1., six different batches of crude material of varying amounts of Compound of Formula I were combined such that the combination has an average of 91% of Compound of Formula I. The combination was dissolved in methanol and concentrated by rotary evaporation. The concentrated solution is then mixed with isopropanol, filtered, and dried by vacuum to produce a white powder with a melting point of 156-160° C.

X-ray powder diffraction of the white powder is shown in FIG. 6 comprising 2 theta values of 7.5°, 15.4°, and 18.7°.

7.4.3. Illustrative Example 3 of the Preparation of a Polymorph of R-Tiacumicin Preparation of Polymorph B from Chloroform After the fermentation process as described for example in Section 7.1., a crude material of tiacumicins containing Compound of Formula I was dissolved in chloroform and concentrated by evaporation at room temperature to produce a solid with a melting point of 156-160° C.

7.4.4. Illustrative Example 4 of the Preparation of a Polymorph of R-Tiacumicin Preparation of a Polymorphic Form from Acetone After the fermentation process as described for example in Section 7.1., a crude material of tiacumicins containing Compound of Formula I was dissolved in acetone and concentrated by evaporation at room temperature to produce a solid with a melting point of 156-160° C.

7.5. Preparation of Amorphous Forms of Compound of Formula I

Preparation of Amorphous Mixture of Tiacumicins

The amorphous mixture of tiacumicins was obtained after column purification without any further processing steps. Alternatively, chloroform or acetone may be added to the mixture of tiacumicins and the solvent is evaporated to form the amorphous product.

X-ray powder diffraction of the product exhibits no defined diffraction peaks.

8. EXPERIMENTAL DATA

8.1. Polymorph Experimental Data

A first polymorph of a Compound of a Compound of Formula I is characterized by Differential Scanning Calorimetry ("DSC") and powder X-Ray Diffraction ("XRD").

The DSC plot of the polymorph shows an endothermic curve at 177° C.

The XRD diagram (reported in FIG. 1) shows peaks comprising at diffraction angles 2θ of 7.7°, 15.0°, 18.8°. The XRD was analyzed with a Phillips powder Diffractometer by scanning from 20 to 70 degrees two-theta at 1.0 degree per minute using Cu K-alpha radiation, at 35 kV and 20 ma. The instrumental error (variant) is 0.04 (2 theta value).

The melting point of the mixtures containing various amounts of Compound of Formula I is summarized in Table 1. All of the products with at least 85% of a Compound of Formula I in the form of a polymorph appear to have a melting point in the range of 163-169° C. measured by Melting Point apparatus, MEL-TEMP 1001.

TABLE 1

Melting point of polymorph mixtures in different solvent conditions

| No. | Compound of Formula I Content (%) of the crystalline material | Mp (° C.) | Crystallization Solvent |
|---|---|---|---|
| 1 | 85 | 165-169 | MeOH/Water |
| 2 | 85 | 163-165 | Isopropanol |
| 3 | 85 | 164-168 | Acetonitrile |
| 4 | 90 | 165-168 | MeOH/Isopropanol |
| 5 | 94 | 166-169 | MeOH/Water |
| 6 | 95 | 166-169 | MeOH/Water |
| 7 | 98 | 163-164 | MeOH/Isopropanol |

Composition of the a polymorphic crystal from a mixture comprising Compound of Formula I and optionally at least on compound that is a mixture of tiacumicins based on HPLC analysis with a melting point of 166-169° C.

X-ray diffraction of a polymorphic crystal shows characteristic peaks at angles 2θ of 7.8°, 15.0°, 18.8°, and 23.9°. Table 2 is a listing of the obtained X-ray diffraction peaks for first polymorph of R-Tiacumicin from Experiment 7.2.2.

TABLE 2

X-ray diffraction peaks for a First Polymorph from Experiment 7.3.2.

| Two-Theta | Relative Intesity |
|---|---|
| 3.3568 | 44.0000 |
| 3.4400 | 47.0000 |
| 7.7815 | 112.0000 |
| 10.1575 | 32.0000 |
| 13.6023 | 21.0000 |
| 15.0951 | 139.0000 |
| 17.0178 | 18.0000 |
| 18.8458 | 36.0000 |
| 19.3771 | 9.0000 |
| 20.0300 | 16.0000 |
| 20.4842 | 10.0000 |
| 23.9280 | 136.0000 |
| 24.8338 | 10.0000 |
| 25.0889 | 19.0000 |
| 25.7256 | 10.0000 |
| 30.9126 | 75.0000 |

TABLE 2-continued

X-ray diffraction peaks for a First Polymorph from Experiment 7.3.2.

| Two-Theta | Relative Intesity |
|---|---|
| 31.9970 | 10.0000 |
| 34.4507 | 30.0000 |

Table 3 is a listing of the obtained X-ray diffraction peaks for Polymorph from Experiment 7.3.6.

TABLE 3

X-ray diffraction peaks for a Polymorph from Experiment 7.3.6.

| Two-Theta | Relative Intensity |
|---|---|
| 3.2978 | 41.0000 |
| 7.5615 | 400.0000 |
| 9.9482 | 21.0000 |
| 15.4289 | 31.0000 |
| 22.0360 | 20.0000 |
| 22.5361 | 20.0000 |
| 24.9507 | 12.0000 |
| 29.5886 | 10.0000 |
| 34.8526 | 19.0000 |
| 37.7092 | 17.0000 |
| 40.4361 | 13.0000 |
| 42.2446 | 18.0000 |

8.2. Second Polymorph of R-Tiacumicin Experimental Data

A second polymorph of Compound of Formula I is also characterized by Differential Scanning Calorimetry (DSC) and powder X-Ray Diffraction (XRD).

The DSC plot of polymorph B shows an endothermic curve at 158° C. The XRD diagram shows peaks comprising at the values of the diffraction angles 2-theta of 7.6°, 15.4° and 18.8°. Polymorph B has a melting point in the range of 153-156° C. measured by Melting Point apparatus, MEL-TEMP 1001.

It is believed that crystalline polymorphic forms of Compounds of Formula I other than the above-discussed A and B exist and are disclosed herein. These crystalline polymorphic forms, including A and B, and the amorphous form or mixtures thereof contain varying amounts of Compound of Formula I and in certain cases mixtures of tiacumicins can be advantageously used in the production of medicinal preparations having antibiotic activity.

X-ray powder diffraction of the crystals shows peaks at angles 2θ of 7.5°, 15.7°, and 18.9°±0.04 indicating the presence of Polymorph B.

The DSC plot of Polymorph B shows an endothermic curve starting at about at 150° C. and peak at 158° C.

Table 4 is a summary of the various data that was isolated for illustrative crystallization lots.

TABLE 4

Data Summarizing Various Lots

| No. | Compound of Formula I Content (%) | Mp (° C.) | DSC Peak (° C.) | XRD (2 theta) | Crystallization Solvent |
|---|---|---|---|---|---|
| 1 | 76.3 | 155-158 | | 7.7, 15.0, 18.8, | MeOH/Water |
| 2 | 85.3 | 159-164 | 180 | 7.8, 14.9, 18.8, | MeOH/Water |
| 3 | 85.4 | 163-165 | | 7.6, 15.4 | Iso-propanol (IPA) |
| 4 | 85.4 | 164-168 | | 7.9, 15.0, 18.8 | Acetonitrile |
| 5 | 85.4 | 153-156 | | 7.5, 15.7, 18.9 | EtOAc |
| 6 | 90 | 165-168 | | 7.5, 15.2, 15.7, 18.6 | MeOH/Isopropanol |
| 7 | 97.2 | 160-163 | 177 | 7.4, 15.4, 18.7 | IPA |
| 8 | 94.0 | 166-169 | 177 | 7.6, 15.1, 18.6 | MeOH/Water |
| 9 | 97.2 | 167-173 | 187 | 7.8, 14.8, 18.8 | MeOH/Water |
| 10 | 96.7 | | 160 | 7.5, 15.4, 18.8 | EtOAc |
| 11 | 98.3 | 163-164 | 178 | 7.7, 15.0, 18.8 | MeOH/IPA |

The present invention is not to be limited in scope by the specific embodiments disclosed in the examples which are intended as illustrations of a few aspects of the invention and any embodiments which are functionally equivalent are within the scope of this invention. Indeed, various modifications of the invention in addition to those shown and described herein will become apparent to those skilled in the art and are intended to fall within the appended claims.

A number of references have been cited, the entire disclosures of which are incorporated herein by reference.

What is claimed is:

1. A method of treating a bacterial infection in a subject in need thereof comprising administering to said subject a therapeutically effective amount of a composition comprising a polymorphic form of a compound of Formula I:

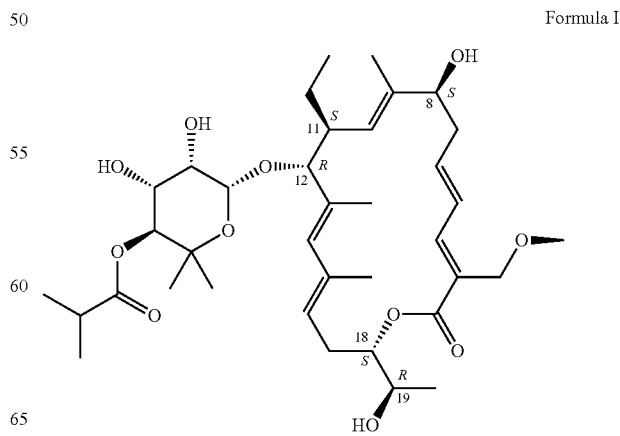

Formula I

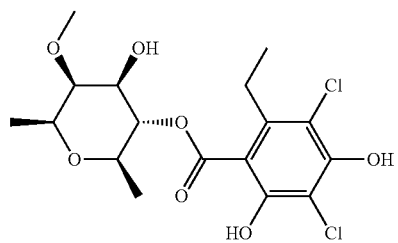

characterized by a powder x-ray diffraction pattern comprising peaks at diffraction angles 2θ of 7.6°, 15.4°, and 18.8°±0.1.

2. The method of claim 1, wherein the administration is oral.

3. The method of claim 1, wherein the amount is from about 0.001 mg to about 1000 mg.

4. The method of claim 1, wherein the composition comprising a polymorphic form of a compound of Formula I is a solid dosage form.

5. The method of claim 1, wherein the polymorphic form of a compound of Formula I is present in at least about 75% to about 99.99% of the total weight.

6. The method of claim 1, wherein the polymorphic form of a compound of Formula I is present in at least about 85% of the total weight.

7. The method of claim 1, wherein the polymorphic form of a compound of Formula I is present in at least about 90% of the total weight.

8. The method of claim 1, wherein the polymorphic form of a compound of Formula I is present in at least about 95% of the total weight.

9. The method of claim 1, wherein the polymorphic form of a compound of Formula I is present in at least about 99% of the total weight.

10. The method of claim 1, wherein the bacterial infection is caused by enterococci, vancomycin resistant enterococci, clostridia, *Clostridium perfringen,* or *Clostridium difficile.*

11. The method of claim 10, wherein the bacterial infection is caused by *Clostridium difficile.*

12. A method of treating a gastrointestinal infection in a subject in need thereof comprising administering to said subject a therapeutically effective amount of a composition comprising a polymorphic form of a compound of Formula I:

Formula I

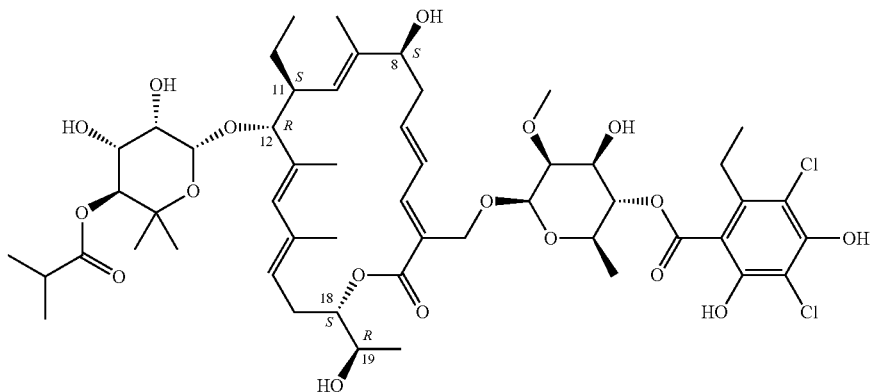

characterized by a powder x-ray diffraction pattern comprising peaks at diffraction angles 2θ of 7.6°, 15.4°, and 18.8°±0.1.

13. The method of claim 12, wherein the administration is oral.

14. The method of claim 12, wherein the amount is from about 0.001 mg to about 1000 mg.

15. The method of claim 12, wherein the composition comprising a polymorphic form of a compound of Formula I is a solid dosage form.

16. The method of claim 12, wherein the polymorphic form of a compound of Formula I is present in at least about 75% to about 99.99% of the total weight.

17. The method of claim 12, wherein the polymorphic form of a compound of Formula I is present in at least about 85% of the total weight.

18. The method of claim 12, wherein the polymorphic form of a compound of Formula I is present in at least about 90% of the total weight.

19. The method of claim 12, wherein the polymorphic form of a compound of Formula I is present in at least about 95% of the total weight.

20. The method of claim 12, wherein the polymorphic form of a compound of Formula I is present in at least about 99% of the total weight.

21. The method of claim 12, wherein the gastrointestinal infection is caused by enterococci, vancomycin resistant enterococci, clostridia, *Clostridium perfringen,* or *Clostridium difficile.*

22. The method of claim 21, wherein the gastrointestinal infection is caused by *Clostridium difficile.*

23. The method of claim 12, wherein the gastrointestinal infection is *C. difficile* infection.

24. A method of treating *C. difficile* infection in a subject in need thereof comprising administering to said subject a therapeutically effective amount of a composition comprising a polymorphic form of a compound of Formula I:

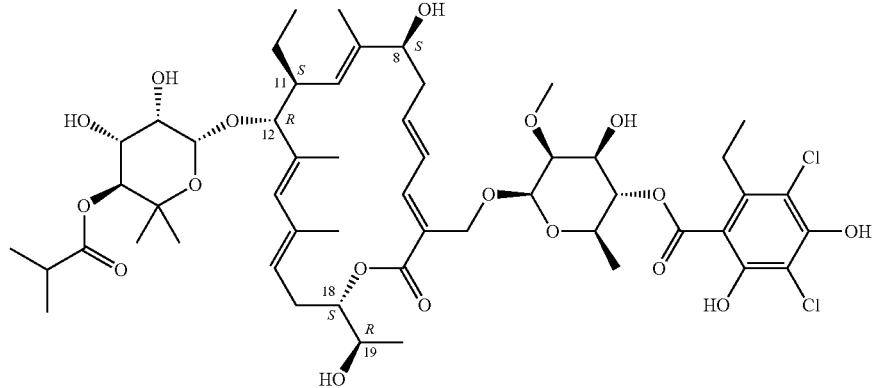

Figure 2:
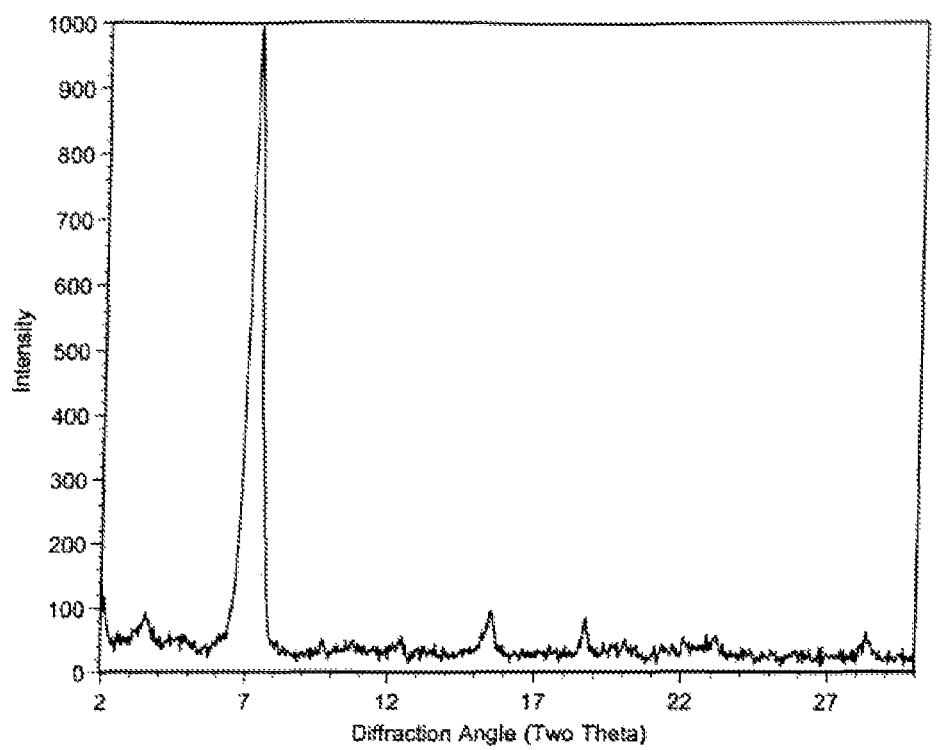
FIG. 2 shows the X-ray powder diffraction patterns of a second polymorph Compound of Formula I produced from ethyl acetate.

Formula I characterized by a powder x-ray diffraction pattern comprising peaks at diffraction angles 2θ of 7.6°, 15.4°, and 18.8°±0.1 as set forth in FIG. 2.

* * * * *

UNITED STATES PATENT AND TRADEMARK OFFICE
CERTIFICATE OF CORRECTION

PATENT NO. : 8,518,899 B2  
APPLICATION NO. : 12/552919  
DATED : August 27, 2013  
INVENTOR(S) : Yu-Hung Chiu et al.

Page 1 of 1

It is certified that error appears in the above-identified patent and that said Letters Patent is hereby corrected as shown below:

In the Specification

Figure 1:
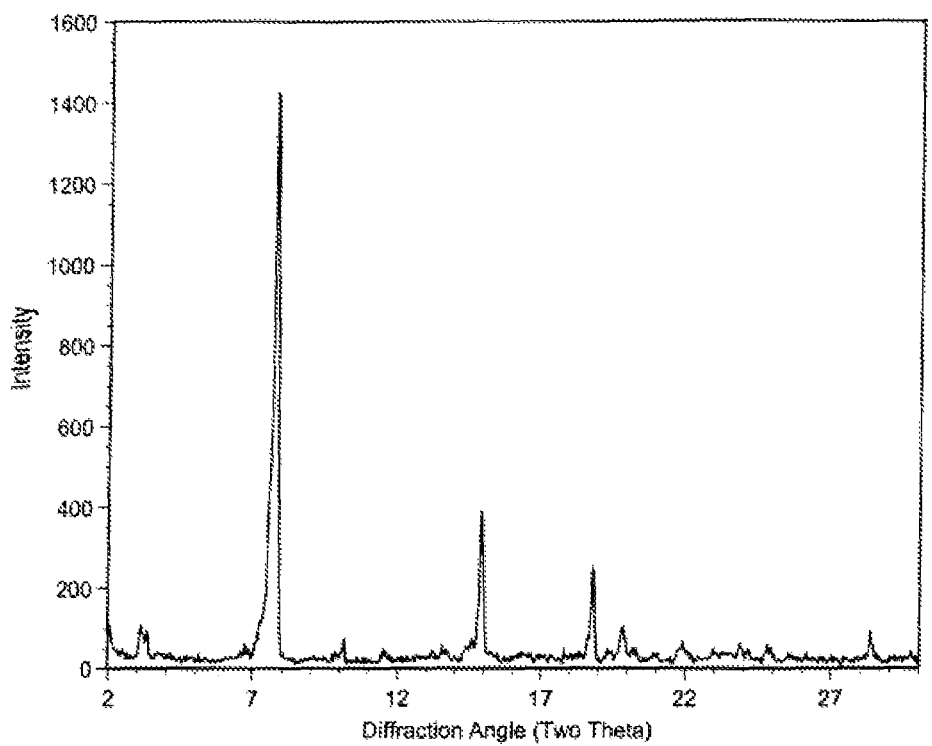
FIG. 1 shows the X-ray powder diffraction patterns of a first polymorph Compound of Formula I produced from methanol and water.

In column 27, line 57, delete "FIG. 3 included 2θ of 7.7°, 15.0°, and 18.8°" and insert --FIG.1 included 2θ of 7.7°, 15.0°, and 18.8°--

In column 29, lines 33-34, delete "is shown in FIG. 6 comprising" and insert --comprises--

In the Claims

In claim 1 (from column 32, line 48 to column 33, line 14), Formula I should appear as follows:

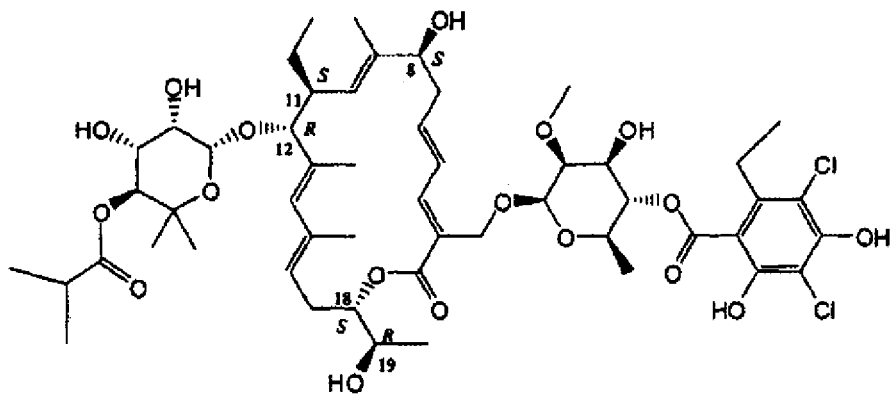

Signed and Sealed this  
Eighteenth Day of March, 2014

Michelle K. Lee  
*Deputy Director of the United States Patent and Trademark Office*